United States Patent
Gershteyn et al.

(12)

(10) Patent No.: US 6,348,694 B1
(45) Date of Patent: Feb. 19, 2002

(54) METHOD AND APPARATUS FOR DETERMINING AN ABILITY OF SKIN TO WITHSTAND EXPOSURE TO HARMFUL RADIATION, AND A SAFE EXPOSURE TIME OF THE SKIN

(76) Inventors: Mikhail Gershteyn, 41 Dedham St., Newton, MA (US) 02461; Elliot Gershtein, 209 Riverview Ave. #7, Newton, MA (US) 02466; Alexander Schechter, 900 Lexington #1-9, Waltham, MA (US) 02452

( * ) Notice: Subject to any disclaimer, the term of this patent is extended or adjusted under 35 U.S.C. 154(b) by 0 days.

(21) Appl. No.: 09/344,167
(22) Filed: Jun. 24, 1999
(51) Int. Cl.⁷ .................................................. G01J 1/42
(52) U.S. Cl. ...................................................... 250/372
(58) Field of Search .......................................... 250/372

(56) References Cited

U.S. PATENT DOCUMENTS

| | | | |
|---|---|---|---|
| 4,229,733 A | 10/1980 | Tulenko et al. | 340/500 |
| 4,749,865 A | 6/1988 | Scheller | 250/338 |
| 4,851,686 A | 7/1989 | Pearson | 250/372 |
| 4,882,598 A | * 11/1989 | Wulf | 250/338.1 |
| 4,962,910 A | 10/1990 | Shimizu | 250/372 |
| 4,985,632 A | 1/1991 | Bianco et al. | 250/372 |
| 5,008,548 A | * 4/1991 | Gat | 250/372 |
| 5,107,123 A | 4/1992 | Shi | 250/372 |
| 5,151,600 A | 9/1992 | Black | 250/372 |
| 5,533,509 A | * 7/1996 | Koashi et al. | 128/633 |
| 5,612,541 A | 3/1997 | Hoffmann et al. | 250/474.1 |
| 5,640,957 A | 6/1997 | Kaminski et al. | 128/653.1 |

OTHER PUBLICATIONS

Web–Site Disclosure, SafeSun, Personal UV Meter, http://lessemf.com/199.html, pp. 1–5, Apr. 12, 1999.

Web–Site Disclosure, SafeSun, Personal UV Meter, Features, http://www.safesun.com/features.html, pp. 1–2, May 20, 1999.

Web–Site Disclosure, SafeSun, Personal UV Meter, Skin and SPF, http://www.safesun.com/skin.html, pp. 1–2, May 20, 1999.

* cited by examiner

*Primary Examiner*—Constantine Hannaher
*Assistant Examiner*—Shun Lee (57) ABSTRACT

Various methods and apparatus for determining an ability of a region of skin to withstand exposure to harmful radiation, as well as a safe exposure time of the skin to harmful radiation, are disclosed. In various embodiments, methods and apparatus according to the invention provide real time information about the cumulative effects of exposure to harmful radiation, such as ultraviolet radiation, based on an individual's skin type, or "natural" protection factor, and the actual effectiveness of any sunscreen applied on the individual's skin, independently of the labeled sun protection factor (SPF) of the sunscreen. In one embodiment, the invention periodically measures the individual's skin darkness (natural protection factor), the dynamic actual effectiveness of sunscreen, if applied, and a total exposure level of the skin to potentially harmful radiation, and determines a safe exposure time of the skin to the radiation. The safe exposure time may be continuously updated based on changes in skin darkness, sunscreen efficiency, and total exposure level over time.

5 Claims, 6 Drawing Sheets

METHOD AND APPARATUS FOR DETERMINING AN ABILITY OF SKIN TO WITHSTAND EXPOSURE TO HARMFUL RADIATION, AND A SAFE EXPOSURE TIME OF THE SKIN

FIELD OF THE INVENTION

This invention relates to exposure of skin to harmful radiation, and more particularly, to methods and apparatus for determining both an ability of the skin to withstand exposure to the harmful radiation, as well as a safe exposure time of the skin to the harmful radiation.

BACKGROUND OF THE INVENTION

Radiation emanated by the sun, commonly referred to as "sunlight," is composed of many different wavelengths of electromagnetic radiation. The spectrum of radiation constituting sunlight may be categorized generally into infrared energy wavelengths, visible light wavelengths, and ultraviolet light wavelengths. Infrared energy typically includes wavelengths above approximately 760 nanometers. Visible light typically includes wavelengths in a range of from approximately 400 nanometers to 760 nanometers. Ultraviolet light typically includes wavelengths below approximately 400 nanometers.

Over the years, scientists, medical researchers, and the like have discovered that humans are susceptible to a variety of internal and external bodily damage from exposure to various wavelength ranges of radiation. In particular, researchers have discovered that humans are among the living beings most vulnerable to a number of ailments associated with exposure to ultraviolet radiation. Excessive exposure to ultraviolet radiation has been linked to skin cancer, cataracts in human eyes, sunburn, skin wrinkling, and other external and internal bodily damage. While, in the past, the earth's ozone layer acted as a natural filter for ultraviolet radiation emanated by the sun, thereby limiting potentially harmful ultraviolet rays from reaching the earth's surface, a decrease in the earth's ozone layer in recent years has resulted in an increased exposure of the earth's surface to ultraviolet radiation.

The potentially harmful effects of over-exposure to various harmful radiation, such as ultraviolet radiation, pose a particularly insidious threat to humans. For example, in general, long-term damage caused by ultraviolet radiation may begin in early years, with sunburns that occur during childhood and the teenage years. Notwithstanding early exposure, however, the cumulative effects of exposure to ultraviolet radiation generally do not begin to manifest themselves until mid-life, between the ages of 40 to 60, when it is often too late to rectify such damage and prevent further damage.

Many medical professionals believe that skin cancer has become one of the most widespread forms of cancer today, as a result of the decrease in the earth's ozone layer and early over-exposure to ultraviolet radiation. It is currently estimated that over one million people in the United States develop different types of skin cancer every year. Although skin cancer is generally considered as one of the mildest forms of cancer, approximately 7% of those people afflicted with skin cancer die as a result. In some areas of the world, for example, the United Kingdom, skin cancer is currently the second most common form of cancer.

Wavelength ranges of ultraviolet radiation which are potentially harmful, as well as threshold limits of exposure intensity associated with such wavelength ranges, have been studied by the American Conference of Governmental Industrial Hygienists (ACGIH). The ACGIH, as well as other health related organizations world-wide, have determined that the most harmful ultraviolet wavelengths are in a range from approximately 200 nanometers to 320 nanometers. Threshold limit values for exposure to these ultraviolet wavelengths have been set forth in the publication "Documentation of the Threshold Limit Values and Biological Exposures Indices," American Conference of Governmental Industrial Hygienists, Pub. No. 0206, ISBN: 0-936712-96-1, pp. 671–674. Additionally, the Diffey Erythema Sensitivity Spectrum, which was developed to describe the relative sensitivities of human skin in general to particular ultraviolet wavelengths, has been accepted throughout the world as a generic indicator of human susceptibility to harm from ultraviolet radiation.

As discussed above, due to the filtering function of the earth's ozone layer, the intensity of ultraviolet radiation emanated by the sun and reaching the earth's surface is not uniform throughout the ultraviolet wavelength spectrum. By considering both the spectrum of ultraviolet radiation that actually reaches the earth's surface through the ozone layer, in combination with the Diffey Erythema Sensitivity Spectrum of relative human sensitivity to ultraviolet wavelengths, an "effective ultraviolet spectrum" can be constructed for humans on the earth's surface. Such an effective ultraviolet spectrum reveals that the particular ultraviolet wavelengths most harmful to humans are in a narrow range of from approximately 300 nanometers to 320 nanometers. This ultraviolet wavelength range is commonly referred to as UV-B. It should be appreciated, however, that other wavelength ranges, including other ultraviolet ranges such as UV-A (from approximately 320 nanometers to approximately 400 nanometers), may be potentially harmful to humans.

To reduce ultraviolet radiation exposure, it is common to apply a sunscreen, or an ultraviolet radiation blocking cream, to the skin. In general, while some types of sunscreen are designed to reflect ultraviolet radiation to some extent, other more common types of sunscreen contain ultraviolet radiation absorbers, which absorb or "block" part or most of the harmful ultraviolet radiation to prevent it from reaching the skin, depending upon the amount of the absorbers present in the sunscreen. Many sunscreens, however, whether reflecting or absorbing, do not completely block ultraviolet radiation and, in particular, allow some of the harmful UV-B range of ultraviolet wavelengths to reach the skin. Additionally, while most sunscreens are labeled with a generic "sun protective factor," or SPF, it is often difficult to ascertain the actual effectiveness of the sunscreen, as well as the actual total exposure level to harmful ultraviolet radiation, with respect to a particular individual.

Several medical professionals have suggested that the probability of an individual to develop skin cancer, or other ailments associated with exposure to ultraviolet radiation, likely depends on several "personal" factors, in addition to the level of harmful ultraviolet radiation reaching the earth's surface to which the individual is exposed. Examples of other factors that likely affect an individual's propensity to suffer harm from over-exposure to ultraviolet radiation include the total exposure time to ultraviolet radiation, any personal or family history of skin-related and/or cancer-related ailments, and an individual's skin type or "darkness." In particular, the risk of developing skin cancer or other ultraviolet radiation related damage may be higher, for example, for more fairly-skinned people who may freckle or burn easily, or those with more lightly colored hair.

Another potentially significant factor that affects an individual's propensity to suffer harm from over-exposure to ultraviolet radiation relates to the actual effectiveness of any sunscreen applied to the particular individual's skin, given other personal characteristics of the individual, such as skin darkness. The generic sun protection factor (SPF) with which most sunscreens are typically labeled merely indicates a multiplication factor of protection against ultraviolet radiation, based on any "natural" protection afforded by human skin itself. For example, an SPF of 15 suggests protection from ultraviolet radiation on the order of approximately 15 times that of the natural protection afforded by human skin.

However, there may be several instances in which the actual SPF of a sunscreen applied to a region of skin may be different than a labeled SPF of the sunscreen. For example, one factor related to the effectiveness of sunscreen applied to an individual's skin is how thickly the sunscreen is applied to the skin, which may vary from individual to individual, and from application to application. Different thicknesses of sunscreen applications contain different amounts of ultraviolet reflectors or absorbers, and hence provide different amounts of protection.

Additionally, sunscreens generally do not become effective until they have dried to some extent after application; hence, an individual may mistakenly believe that they are protected once they have applied the sunscreen, but in fact may by harmfully exposed to ultraviolet radiation throughout a drying period (typically 15–20 minutes) of the sunscreen after application.

Moreover, once effective, sunscreens are generally effective for only a finite period, and lose their effectiveness, or "age," over time with continued exposure. Accordingly, while an individual may initially apply a sufficient amount of sunscreen and wait an appropriate drying time before exposing themselves to ultraviolet radiation, as the sunscreen "ages" the individual may mistakenly believe that they are still fully protected, when in fact the effectiveness of the sunscreen has deteriorated to some extent. Additionally, sunscreens generally have a limited "shelf-life," and their effectiveness "expires" after some time period, irrespective of exposure to ultraviolet radiation. Accordingly, an individual may apply sunscreen that is close to or past an "expiration date" without realizing that the sunscreen is no longer fully capable of providing protection against potentially harmful ultraviolet radiation.

Additionally, one potential problem with a generic characterization of sunscreens using an SPF rating is that the natural protection afforded by the skin will vary depending upon a particular individual's skin type or darkness; accordingly, the SPF rating of the sunscreen is generally not an accurate reflection of an actual protection against exposure to potentially harmful radiation for many people. Furthermore, dynamic changes of the ultraviolet radiation to which the individual is exposed over time may also in part determine an individual's ability to withstand exposure to radiation and, as a result, a safe exposure time.

SUMMARY OF THE INVENTION

The present invention is directed to various methods and apparatus for determining an ability of a region of skin to withstand exposure to harmful radiation, as well as a safe exposure time of the region of skin to the harmful radiation, including ambient ultraviolet radiation.

In one embodiment, an apparatus according to the invention includes a first detector to detect an ability of a region of skin to withstand exposure to harmful radiation, a second detector to detect a level of the harmful radiation to which the region of skin is exposed, and a first circuit, coupled to the first and second detectors, to calculate a safe exposure time based on the ability of the region of skin to withstand the exposure to the harmful radiation and the level of the harmful radiation.

In another embodiment, an apparatus according to the invention includes a first radiation path to direct first radiation and second radiation to a region of skin on which sunscreen has been applied. The first radiation has at least one first wavelength within an absorption spectrum of the sunscreen, and the second radiation has at least one second wavelength not within the absorption spectrum of the sunscreen. The apparatus further includes at least one radiation sensor to detect the first radiation and the second radiation reflected from the region of skin, and a first circuit, coupled to the at least one radiation sensor, to determine an effectiveness of the sunscreen based on the reflected first radiation and the reflected second radiation.

In another embodiment, an apparatus to measure a natural protection factor of a region of skin according to the invention includes a radiation path to direct radiation to the region of skin, at least one reference sensor to detect the radiation incident to the region of skin and output a reference signal based on the incident radiation, at least one radiation sensor to detect the radiation reflected from the region of skin and to output a radiation signal based on the reflected radiation, and a circuit, coupled to the at least one reference sensor and the at least one radiation sensor, to output a skin darkness signal based on the reference signal and the radiation signal, wherein the natural protection factor is based on the skin darkness signal.

In another embodiment, an apparatus to measure a total protection factor of a region of skin exposed to harmful radiation according to the invention includes a first circuit to measure a natural protection factor of the region of skin, and a second circuit to measure an effectiveness of sunscreen applied to the region of skin, wherein the total protection factor is based on the natural protection factor and the effectiveness of the sunscreen.

In another embodiment, an apparatus to measure a level of radiation to which a region of skin is exposed according to the invention includes at least one detector to detect the radiation directly incident to the region of skin and the radiation reflected from at least one surface prior to the radiation irradiating the region of skin, and a circuit, coupled to the at least one detector, to output at least one exposure level signal based on the directly incident radiation and the reflected radiation.

In another embodiment, a method for determining a safe exposure time of a region of skin exposed to harmful radiation according to the invention includes steps of measuring an ability of the region of skin to withstand exposure to the harmful radiation, measuring a level of the harmful radiation, and calculating a safe exposure time based on the ability of the region of skin to withstand the exposure to the harmful radiation and the level of the harmful radiation.

In another embodiment, a method for determining an effectiveness of sunscreen applied to a region of skin according to the invention includes steps of irradiating the region of skin with first radiation having at least one first wavelength within an absorption spectrum of the sunscreen, irradiating the region of skin with second radiation having at least one second wavelength outside the absorption spectrum of the sunscreen, measuring a first reflected level of the first radiation reflected from the region of skin, measuring a second reflected level of the second radiation reflected from the region of skin, and determining the effectiveness of the sunscreen based on the first reflected level and the second reflected level.

In another embodiment, a method for measuring a natural protection factor of a region of skin according to the invention includes steps of irradiating the region of skin with radiation, measuring an incident level of the radiation incident to the region of skin, measuring a reflected level of the radiation reflected from the region of skin, and determining the natural protection factor of the region of the skin based the reflected level and the incident level.

In another embodiment, a method for measuring a total protection factor of a region of skin exposed to harmful radiation includes steps of measuring a natural protection factor of the region of skin, measuring an effectiveness of sunscreen applied to the region of skin, and determining the total protection factor based on the natural protection factor and the effectiveness of the sunscreen.

In another embodiment, a method for measuring a level of radiation to which a region of skin is exposed according to the invention includes steps of detecting the radiation directly incident to the region of skin, and detecting the radiation reflected from at least one surface prior to the radiation irradiating the region of skin.

Other advantages, novel features, and objects of the invention will become apparent from the following detailed description of the invention, when considered in conjunction with the accompanying drawings.

BRIEF DESCRIPTION OF THE DRAWINGS

The accompanying drawings are not intended to be drawn to scale. In the drawings, each identical or nearly identical component that is illustrated in various figures is represented by a like reference character or numeral. For purposes of clarity, not every component may be labeled in every drawing. In the drawings.

DETAILED DESCRIPTION

The present invention is directed to various methods and apparatus for determining an effectiveness of sunscreen applied to skin, as well as a safe exposure time of the skin to harmful radiation, for example, ultraviolet radiation.

In various embodiments, methods and apparatus according to the invention provide real time information about the actual effectiveness of sunscreen applied on the individual's skin. According to one aspect of these embodiments, radiation in two different wavelength ranges is utilized to determine sunscreen effectiveness and safe exposure time. For example, a first wavelength range within an absorption spectrum of the sunscreen, and a second wavelength range outside the absorption spectrum, can be applied to the skin to measure the effectiveness of sunscreen applied thereon. According to another aspect of these embodiments of the invention, a safe exposure time to the sun may be determined based upon the measured effectiveness of the sunscreen. In a further aspect, the effectiveness of the sunscreen may be periodically measured over time to determine a dynamic behavior of the sunscreen with continued exposure to ultraviolet radiation, and a safe exposure time to the harmful radiation may be continuously updated based on changes in the effectiveness of the sunscreen and environmental conditions affecting the total exposure level over time.

In another embodiment of the invention, a wavelength range can be used to dynamically measure the overall ability of the skin (whether or not having sunscreen applied thereon) to withstand exposure to harmful radiation. This overall effectiveness of the skin to withstand harmful radiation may be periodically measured over time to determine a dynamic behavior of the skin (with or without sunscreen) with continued exposure to ultraviolet radiation, and a safe exposure time may be continuously updated based on changes in the effectiveness of the skin to withstand the harmful radiation and changes in environmental conditions affecting the total exposure level over time.

In another illustrative embodiment, an apparatus according to the invention measures the ability of a region of an individual's skin to withstand exposure to harmful radiation, for example an individual's skin darkness as well as a dynamic actual effectiveness of any sunscreen applied to the skin, and a total exposure level of the skin to the harmful radiation, and determines a safe exposure time of the skin to the harmful radiation. In one aspect of this embodiment, the safe exposure time may be continuously updated based on changes in the ability of the individual's skin to withstand exposure to the harmful radiation, and environmental conditions affecting the total exposure level over time.

In another embodiment of the invention, a number of ambient radiation sensors are employed having planes of incidence at various orientations to detect ambient radiation at a number of incidence angles. The ambient radiation sensors may be arranged such that ambient radiation from several directions may be detected from various locations proximate to the skin. For example, two or more ambient radiation sensors may be spaced apart, or distributed partially or fully around, an apparatus according to the invention, or may be oriented in different planes on the body of the apparatus. In this manner, the invention is capable of measuring an exposure of the skin to both "direct" ultraviolet radiation, and exposure due to reflections from a variety of surfaces surrounding the skin, such as, for example, water, snow, sand, metallic objects associated with various sporting and/or recreational equipment and accessories, and the like. Accordingly, this embodiment of the invention provides accurate measurements of the total exposure level of the skin to ultraviolet radiation, and hence accurate assessments of safe exposure time based on an actual total exposure level.

Figure 1A:
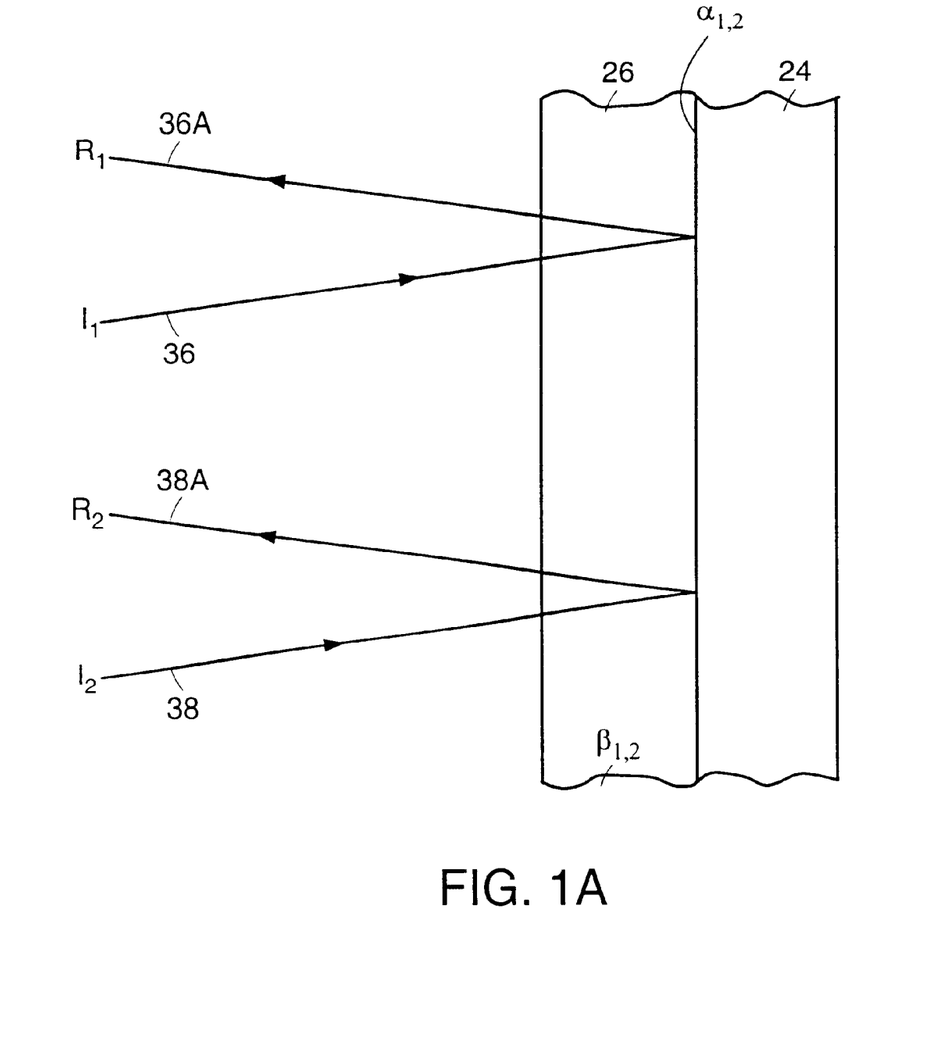
FIG. 1A is a diagram illustrating concepts involving the absorption of radiation which are relevant to various embodiments of the invention.

FIG. 1A is diagram illustrating concepts involving the absorption of radiation which are relevant to various embodiments of the invention. In FIG. 1A, first radiation 36 and second radiation 38 are incident to a region of skin 24 on which sunscreen 26 may be applied. In general, as radiation is incident on matter, one portion of the radiation may be reflected from a surface of the matter, another portion may be absorbed by the matter, and yet another portion may propagate (or be transmitted) through the matter unabsorbed. The foregoing relationship may be simply expressed as:

$$R+A+T=100\% \quad (1)$$

where R denotes a percentage of reflected radiation, A denotes a percentage of absorbed radiation, and T denotes a percentage of transmitted radiation. An analysis of multiple layers of matter each having potentially different reflective, absorptive, and transmissive properties can be quite complicated. However, for the purpose of illustration, the relationship of Eq. (1) can be considered to hold true for a composite structure of layered matter, for example, including the skin 24 and the sunscreen 26.

As shown in FIG. 1A, at least some portion of the first radiation 36 is reflected from the skin 24 as reflected first radiation 36A, and at least some portion of the second radiation 38 is reflected as reflected second radiation 38A. According to one embodiment of the invention, it has been discovered that by measuring the amount of reflected second radiation 38A, methods and apparatus of the invention may determine an absorption factor (or "darkness") of the skin 24 that is indicative of how susceptible the skin 24 is to damage by harmful radiation.

According to another embodiment of the invention, it has been discovered that the effectiveness of the sunscreen 26 can be determined by selecting the first radiation 36 to have a first wavelength range within an absorption spectrum of the sunscreen, and the second radiation 38 to have a second wavelength range outside the absorption spectrum of the sunscreen 26. Additionally, the first and second radiation ranges can be selected so that both are reflected similarly or predictably by the skin 24 (e.g., the first and second radiation wavelengths can be selected so that the reflection of the first radiation 36 by the skin 24 is well-correlated to the reflection of the second radiation 38 by the skin 24). An example of suitable wavelength ranges includes visible and ultraviolet radiation, which respectively fall without and within the absorption spectrum of most sunscreens, and which are both reflected by the skin 24 in a well-correlated manner (as discussed further below).

By irradiating the sunscreen 26 and the skin 24 with the first radiation 36 and the second radiation 38, both of which are reflected similarly by the skin 24, and only one of which (first radiation 36) is significantly absorbed by the sunscreen 26, methods and apparatus according to various embodiments of the invention may advantageously determine an accurate actual effectiveness of the sunscreen 26 in situ, or as applied to the skin 24.

FIG. 1A shows that the incident first radiation 36 has an incident first radiation level $I_1$, and the reflected first radiation 36A has reflected first radiation level $R_1$. Similarly, the incident second radiation 38 has an incident second radiation level $I_2$, and the reflected second radiation 38A has a reflected second radiation level $R_2$. Additionally, FIG. 1A shows that the sunscreen 26 has absorption coefficients $\beta_1$ and $\beta_2$, and the skin 24 has reflection coefficients $\alpha_1$ and $\alpha_2$, wherein the indices "1,2" refer to the wavelength ranges of the first radiation 36 and the second radiation 38, respectively. The reflected first and second radiation levels $R_1$ and $R_2$ represent levels of radiation which is incident to the sunscreen (if applied) and the skin, has passed through the sunscreen to the skin, and has been reflected by the skin.

In general, for purposes of illustration, in FIG. 1A it is assumed that any reflections of the incident first radiation 36 and the incident second radiation 38 from the sunscreen 26 are negligible. Furthermore, it is assumed that the absorption coefficient $\beta_2$ of the sunscreen 26 to the second radiation 38 is essentially one; namely, the second radiation 38 has wavelengths in a range outside the absorption spectrum of the sunscreen 26. Additionally, as discussed above, it is assumed that the reflective properties of the first radiation 36 and the second radiation 38 from the skin 24 are well-correlated, or nearly identical, such that $\alpha_1 \approx \alpha_2$.

In view of the foregoing, the reflected second radiation level $R_2$ may be expressed as:

$$R_2 = I_2 \alpha_2, \quad (2)$$

and the reflected first radiation level $R_1$ may be expressed as:

$$R_1 = I_1 \beta_1^2 \alpha_1, \quad (3)$$

where the absorption coefficient $\beta_1$ in Eq. (3) is squared because the first radiation 36 makes two "passes" through the sunscreen, one pass prior to reflection from the skin 24 and one pass after reflection from the skin. The absorption coefficient $\beta_1$ gives a measure of the effectiveness of the sunscreen 26 to the first radiation 36. In one embodiment in which, for example, the first radiation 36 includes ultraviolet radiation, the absorption coefficient $\beta_1$ gives a measure of an "actual" SPF rating of the sunscreen 26 with respect to ultraviolet radiation.

Accordingly, to measure the effectiveness of the sunscreen 26, first the reflected second radiation level $R_2$ may be measured and compared to the incident second radiation level $I_2$ to obtain the reflection coefficient $\alpha_2$. In some embodiments of the invention, the incident second radiation level $I_2$ may also be measured, while according to other embodiments, the incident second radiation level $I_2$ may be provided from a known source so that it is known a priori, as discussed further below.

It should be appreciated that, since the absorption coefficient $\beta_2$ of the sunscreen 26 to the second radiation 38 is essentially one, Eq. (2) demonstrates that the reflection coefficient $\alpha_2$ of the skin 24, or a measure of skin "darkness," may be determined irrespective of an application of sunscreen. Accordingly, methods and apparatus according to various embodiments of the invention discussed below may determine a skin darkness of an individual, whether or not the individual has applied sunscreen to any region of their skin. It should also be appreciated that if no sunscreen is applied to the skin, a wavelength range of radiation used to determine skin darkness need not be constrained to any particular spectrum.

The measure of skin darkness provided by the reflection coefficient $\alpha_2$ essentially provides an indication of an individual's "natural" protection factor against potentially harmful radiation. Depending on the individual, as a region of skin is continually exposed to the radiation, various amounts of pigment accrue in the skin to absorb potentially harmful radiation. Such pigmentation prevents the harmful radiation from reaching other areas or layers of the skin in which the radiation may cause damage. Some individuals have a greater propensity to accrue pigment, or "tan," which generally results in a higher level of "natural" protection, or a greater ability to withstand exposure to potentially harmful radiation.

The reflection coefficient $\alpha_2$ of the skin is well-correlated to standardized classifications of skin types, as set forth, for example, in a variety of documents published by the United States Environmental Protection Agency (USEPA), and in particular, the article entitled "Sunscreen Drug Products for Over-the-Counter Human Drugs" published in the Federal Register, Vol. 43, No. 166, August 1978, pp 38208–38260, which is herein incorporated by reference. On page 38213 of the aforementioned article, one example of skin type classification based on sensitivity to ultraviolet radiation is given, in which skin types are divided into six categories based on relative "darkness," from pale or extremely sensitive (Type I) to deeply pigmented or essentially insensitive (Type VI). Several such classifications are possible, and the foregoing classification is merely described for purposes of illustration.

Such skin type classifications are associated with minimum doses of radiation, or "minimum erythema doses" (MED), at which some skin damage, such as sunburn, begins to occur. Radiation doses are in turn related to the level of radiation to which the skin is exposed, and the amount of time that the skin is exposed to the radiation. Accordingly, a measure of the reflection coefficient $\alpha_2$ of a region of an individual's skin provides a well-correlated indication of the individual's skin type, or the level of "natural" protection afforded by an individual's skin, and hence may be used to determine a safe exposure time for an individual, based on the level of harmful radiation to which the individual's skin is exposed.

For example, based on the premise that any radiation not absorbed by the skin is essentially reflected from the skin, a higher reflection coefficient $\alpha_2$ generally indicates a lower absorption of radiation by the skin, and hence a lower level of natural protection and a lower skin type classification. In general, skin types having lower classifications, such as Type I for example, require smaller exposure dose levels and shorter exposure times for damage to occur than do skin types having higher classifications, such as Type VI. Accordingly, various methods and apparatus of the invention may utilize the reflection coefficient $\alpha_2$ to determine a safe exposure time based on an individual's skin type, or level or natural protection, alone or in combination with sunscreen. Additionally, according to one embodiment, methods and apparatus of the invention may utilize the reflection coefficient $\alpha_2$ to indicate to an individual their "natural" protection factor relative to, for example, a Type I skin classification, or a highly sensitive skin type.

In FIG. 1A, once the reflection coefficient $\alpha_2$ of the skin 24 is determined according to Eq. (2), the reflection coefficient $\alpha_1$ of the skin 24 to the first radiation 36 is also known, since the first radiation 36 and the second radiation 38 are chosen to have similar, or well-correlated, reflection coefficients in the skin 24. Accordingly, Eq. (3) may be employed to determine the absorption coefficient $\beta_1$ of the sunscreen 26 to the first radiation 36, or an effectiveness of the sunscreen 26 to prevent the incident first radiation 36B from reaching the skin 24, by measuring the reflected first radiation level $R_1$ and comparing it to the incident first radiation level $I_1$. As discussed above, according to some embodiments, the incident first radiation level $I_1$ may also be measured, while according to other embodiments, the incident first radiation level $I_1$ may be known a priori.

For embodiments in which both the first and second incident radiation levels $I_1$ and $I_2$ are known, the absorption factor $\beta_1$ of the sunscreen 26 to the first radiation 36 (i.e., the effectiveness of the sunscreen 26 applied to the skin 24) may be determined based on measurements of the reflected first and second radiation levels $R_1$ and $R_2$. By measuring the first radiation 36A and the second radiation 38A reflected from the skin 24, methods and apparatus of the invention may determine an actual effectiveness of the sunscreen 26 relative to the individual's skin on which the sunscreen 26 is applied, independently of a labeled sun protection factor (SPF) associated with the sunscreen 26. Accordingly, methods and apparatus of the invention may offer several advantages including, but not limited to, allowing an individual to assess if a sufficient amount of sunscreen has been applied, allowing the individual to assess if the sunscreen has "aged" beyond a period of effectiveness or has "expired," and providing the individual with information pertaining to dynamic changes in the individual's ability to withstand exposure to potentially harmful radiation, whether or not sunscreen has been applied.

The concepts outlined above to determine the effectiveness of sunscreen and the ability of skin to withstand exposure to potentially harmful ultraviolet radiation according to the invention may be implemented in several ways, such that the present invention is not limited to any specific implementation. Some examples of specific implementations of the foregoing concepts are provided below for illustrative purposes.

Figure 1B:
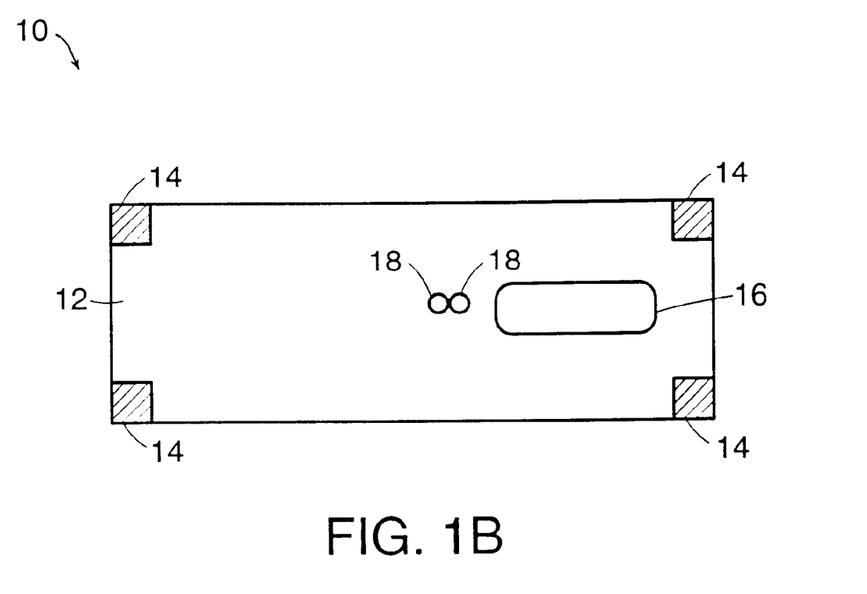
FIG. 1B is a diagram showing a top view of an apparatus for determining an effectiveness of sunscreen applied to skin, according to one embodiment of the invention.

FIG. 1B is a diagram showing a top view of an apparatus 10 for determining an effectiveness of sunscreen applied to skin, according to one embodiment of the invention. In the embodiments shown in FIGS. 1B, 2, and 3, the first radiation 36 and the second radiation 38, discussed above in connection with FIG. 1A, may be derived from ambient radiation, for example, sun radiation. Accordingly, in these embodiments, the incident first and second radiation levels $I_1$ and $I_2$, as indicated in FIG. 1A, are measured by the apparatus 10. In other embodiments of an apparatus according to the invention, the first radiation 36 and the second radiation 38 may be provided from one or more internal or external radiation sources having known power outputs, and hence the incident first and second radiation levels $I_1$ and $I_2$ would be known, as discussed further below.

The apparatus 10 as shown in FIG. 1B includes a front panel 12, which generally faces a source of direct ambient radiation, such as sunlight. FIG. 1B shows that the apparatus 10 may include one or more solar batteries 14, to receive the ambient radiation impinging upon the front panel 12 and to provide power to various components of the apparatus, as discussed further below in connection with FIG. 3. FIG. 1B also shows that the front panel 12 of the apparatus 10 may include one or more radiation path openings 18, which allow the ambient radiation impinging upon the front panel 12 to enter the apparatus 10.

The front panel 12 of the apparatus 10 shown in FIG. 1B may also include one or more indicators 16 to indicate to a user an effectiveness of the sunscreen applied to the user's skin. Examples of indicators 16 suitable for purposes of the invention include, but are not limited to, various liquid crystal displays capable of displaying, for example, alphanumeric characters, various symbols, and bar-type graphs, LEDs or multi-segment LED displays, various audible indicators such as beepers and buzzers, and the like.

Figure 2:
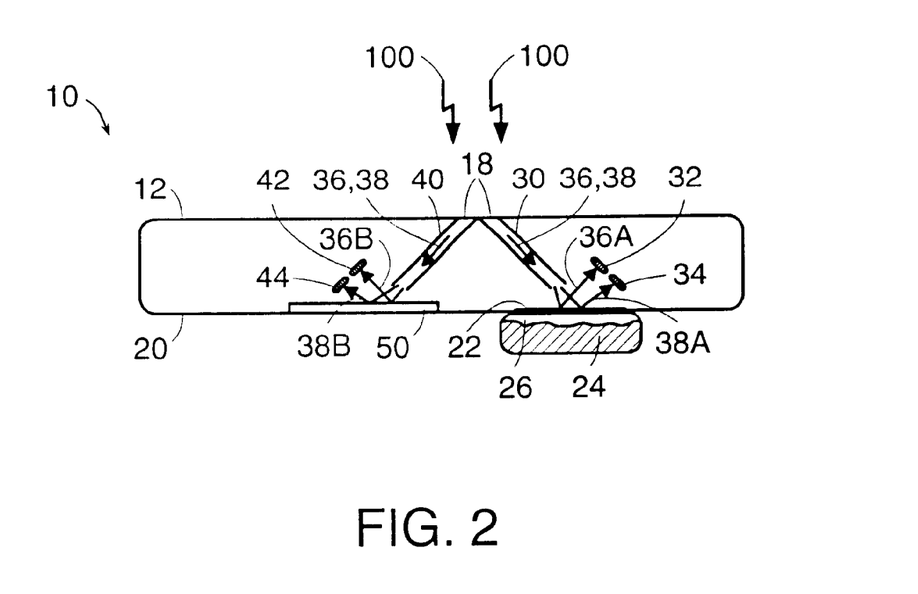
FIG. 2 is a diagram showing a side view of the apparatus of FIG. 1B, according to one embodiment of the invention.

FIG. 2 is a diagram showing a side view of the apparatus of FIG. 1B according to one embodiment of the invention, looking through a "phantom" side panel of the apparatus 10 to various components within the apparatus 10. In the embodiment of FIG. 2, a bottom panel 20 of the apparatus 10 includes a skin window 22, which during normal operation is placed over the skin 24 having the sunscreen 26 applied thereon. The skin window 22 is preferably made of a material which is essentially transparent to radiation in particular wavelength ranges of interest, for example, ultraviolet and visible radiation, as discussed further below.

FIG. 2 also shows that, according to one embodiment of the invention, the apparatus 10 includes a first radiation path 30, coupled to one of the radiation openings 18 on the front panel 12. Examples of radiation paths suitable for purposes of the invention include, but are not limited to, optical guides such as fibers, planar waveguides, or waveguides having various other geometries. The first radiation path 30 directs the ambient radiation 100, which impinges upon the front panel 12 and enters the corresponding radiation path opening 18, to the skin window 22. The radiation 100 directed by the radiation path 30 passes through the skin window 22 to a region of the skin 24 on which the sunscreen 26 has been applied.

As discussed above in connection with FIG. 1A, according to one embodiment of the invention, the radiation 100 passing through the first radiation path 30 includes the first radiation 36, having at least one first wavelength within an absorption spectrum of the sunscreen 26, and the second radiation 38, having at least one second wavelength outside the absorption spectrum of the sunscreen 26. In general, many sunscreens contain ultraviolet radiation absorbers which block part or most of the harmful ultraviolet radiation from reaching the skin 24, depending upon the amount of the absorbers present in the sunscreen 26. Accordingly, most absorbing sunscreens are typically designed to have an absorption spectrum below approximately 400 nanometers.

In particular, many sunscreens are designed to have an absorption spectrum similar to that of the UV-B ultraviolet wavelength range, namely, from approximately 300 nanometers to 320 nanometers. This ultraviolet wavelength range is generally considered to be the most harmful to humans. Other sunscreens may be designed to reflect, rather than absorb, potentially harmful ultraviolet wavelengths, such as those in the UV-B range. Sunscreens which reflect rather than absorb ultraviolet radiation are discussed further below, in connection with other embodiments of the invention.

In view of the foregoing, according to one embodiment of the invention, the first radiation 36 has at least one first wavelength in a range of from approximately 290 nanometers to approximately 320 nanometers. In another embodiment, the first radiation 36 may include one or more wavelengths in a narrower range of from approximately 300 nanometers to approximately 310 nanometers. It should be appreciated that these wavelength ranges are provided merely for illustrative purposes, as the present invention is not limited to use with any particular wavelength range. According to one embodiment, any wavelength range within the absorption spectrum of the sunscreen 26 can be selected for the first radiation 36.

For embodiments of the invention utilizing the ambient radiation 100, such as sun radiation, for example, to provide the first radiation 36 and the second radiation 38, the ambient radiation 100 may include a wide range of wavelengths. Accordingly, the wavelength range of the first radiation 36 and the second radiation 38 is "selected" based on the sensitivites of any sensors used to detect the first and second radiation, as discussed further below.

Alternatively, in embodiments of the invention utilizing radiation sources other than sun radiation, radiation sources may be selected such that the wavelength range of the first radiation 36 is based on the absorption spectrum of a particular type of sunscreen 26 to be analyzed on the skin 24. Additionally, in some embodiments, the first radiation 36 may be narrow-band or essentially monochromatic radiation at a particular wavelength within the absorption spectrum of the sunscreen 26, which is chosen to generally represent the protective characteristics of either a particular sunscreen, or sunscreens in general over a range of wavelengths of interest, such as, for example, the UV-B range.

Unlike the first radiation 36, the second radiation 38, also directed by the radiation path 30 through the skin window 22 to the sunscreen 26 and the skin 24, has at least one second wavelength outside the absorption spectrum of the sunscreen 26. For example, the second radiation 38 may include one or more wavelengths in a range of from approximately 400 nanometers to approximately 760 nanometers, which is a wavelength range typically representative of visible light. It should be appreciated that this wavelength range is provided merely for illustrative purposes, as the present invention is not limited to use with any particular wavelength range. According to one embodiment, any wavelength range outside the absorption spectrum of the sunscreen 26 can be selected for the second radiation 38.

Visible light wavelengths are particularly suitable for the second radiation 38, for, while these wavelengths are generally not absorbed by various sunscreens, the absorption of visible radiation in human skin is well-correlated to the absorption of ultraviolet radiation in human skin. Such a correlation facilitates a determination of sunscreen effectiveness using two different wavelength ranges of radiation, as discussed above in connection with FIG. 1A.

According to one embodiment of the invention, the first radiation 36 and the second radiation 38 directed to the skin 24 and the sunscreen 26 may be derived from, or generated by, a single radiation source emanating each respective wavelength range. In particular, as shown in FIG. 2, the first radiation 36 and the second radiation 38 may be derived essentially from the ambient radiation 100, which, for example, may be sun radiation (sunlight) impinging upon the front surface 12 of the apparatus 10 and entering the radiation path 30 via one of the openings 18.

Alternatively, the apparatus 10 may include one or more internal radiation sources (not shown) to generate the first radiation 36 and the second radiation 38, independently of the ambient radiation 100. In such embodiments, the front panel 12 may not include the radiation path openings 18; instead the first radiation path 30 would be coupled to the one or more internal radiation sources. Examples of internal radiation sources suitable for purposes of the invention include, but are not limited to, a variety of semiconductor sources, such as LEDs, diode lasers, and the like.

As discussed above in connection with FIG. 1A, the incident levels of the first radiation 36 and the second radiation 38 are used as "reference" radiation levels, from which methods and apparatus according to various embodiments of the invention derive information relating to the absorption of one or both of the first radiation 36 and the second radiation 38 by the skin 24, and by any sunscreen 26 that may be applied to the skin. In the case of internal radiation sources or external radiation sources other than sun radiation, for example, such incident levels may easily be derived from known power outputs of the internal or external radiation sources.

Alternatively, whether the apparatus 10 utilizes the ambient radiation 100 or other external or internal radiation sources, the incident levels of the first radiation 36 and the second radiation 38 may be measured externally and then input to the apparatus 10, or may be measured internally by various components of the apparatus 10 itself, as discussed further below. For embodiments in which one or more external or internal radiation sources have known incident levels of radiation, or in which one or more external sources have been measured externally, only radiation reflected from the skin 24 need be measured by the apparatus 10 to determine one or both of sunscreen efficiency and skin darkness.

FIG. 2 also shows that the apparatus 10 includes one or more radiation sensors 32 and 34 to detect the first radiation 36A and the second radiation 38A reflected from the sunscreen 26 and the skin 24. According to one embodiment, the apparatus 10 may include one wide-band radiation sensor capable of detecting both the reflected first radiation 36A and the reflected second radiation 38A. Alternatively, as shown in FIG. 2, two radiation sensors 32 and 34 may be employed to detect the reflected first radiation 36A and the reflected second radiation 38A, respectively.

In general, a variety of radiation sensors having particular sensitivities to the respective wavelength ranges of the first radiation 36 and the second radiation 38 may be suitable for purposes of the invention. In particular, any sensors employed to detect the first radiation 36 may be selected so as to have a sensitivity to wavelength ranges associated with an absorption spectrum of a particular sunscreen, or an absorption spectrum of sunscreens in general. In this manner, various apparatus according to the invention may be tailored to measure the effectiveness of particular sunscreen products, or may be designed to measure the effectiveness of sunscreens in general.

For embodiments of the invention in which levels of radiation incident to the skin 24 and the sunscreen 26 are unknown, FIG. 2 shows that the apparatus 10 may include one or more reference sensors 42 and 44 to detect the first radiation 36 and the second radiation 38 incident to the sunscreen 26 and the skin 24. FIG. 2 also shows that the apparatus 10 may include a second radiation path 40, coupled to one of the radiation path openings 18 on the front panel 12 of the apparatus 10. Similarly to the first radiation path 30, the second radiation path 40 may be an optical guide, such as a fiber, a planar waveguide, or a waveguide having another suitable geometry.

In FIG. 2, the second radiation path 40 directs the incident first radiation 36 and the incident second radiation 38 to the one or more reference sensors 42 and 44, via a reflector 50 that reflects and directs the incident first radiation 36 and the incident second radiation 38 passing through the second radiation path 40 to the reference sensors 42 and 44. The incident first and second radiation reflected by reflector 50 and impinging upon the reference sensors 42 and 44 is indicated in FIG. 2 by the reference characters 36B and 38B, respectively.

While FIG. 2 shows a first reference sensor 42 to detect reflected incident first radiation 36B and a second reference sensor 44 to detect the incident second radiation 38B, the apparatus 10 may utilize one wide-band reference sensor (not shown) to detect both the reflected incident first radiation 36B and the reflected incident second radiation 38B. Additionally, according to one embodiment, the first and second reference sensors 42 and 44 may have sensitivities similar to those of the first and second radiation sensors 32 and 34, as discussed above, and may be selected such that the apparatus 10 is tailored to measure the effectiveness of particular sunscreen products, or the effectiveness of sunscreens in general.

Figure 3:
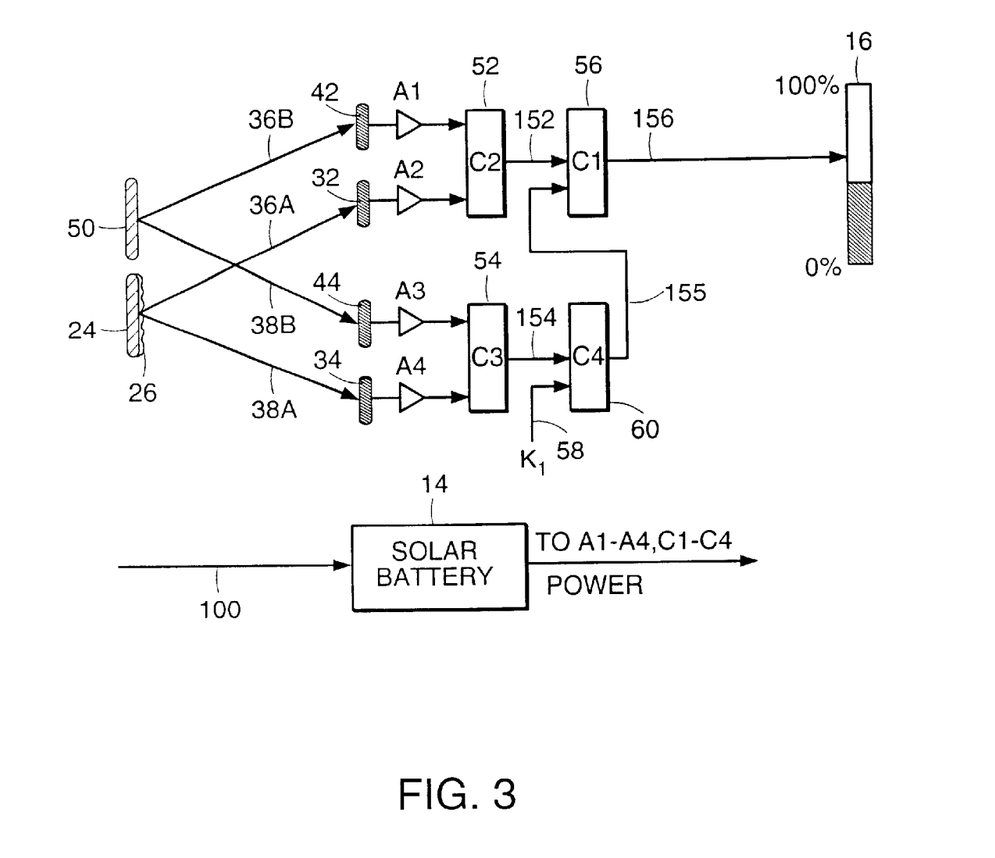
FIG. 3 is a schematic diagram illustrating various components of the apparatus of FIGS. 1B and 2, according to one embodiment of the invention.

FIG. 3 is a schematic diagram illustrating various components to implement the apparatus 10 shown in FIGS. 1 and 2, according to one embodiment of the invention. The embodiment of FIG. 3 shows merely one exemplary implementation of the apparatus 10, and different implementations are possible. Accordingly, the apparatus 10 is not limited to the specific implementation shown in FIG. 3.

In the embodiment of FIG. 3, outputs of radiation sensors 32 and 34 respectively proceed to signal conditioners A2 and A4, which may include, for example, signal amplifiers and filters. The outputs of radiation sensors 32 and 34, and hence outputs of signal conditioners A2 and A4, represent the reflected radiation levels $R_1$ and $R_2$, respectively, discussed above in connection with FIG. 1A.

Similarly, as shown in FIG. 3, outputs of radiation sensors 42 and 44 respectively proceed to signal conditioners A1 and A3, which may include, for example, signal amplifiers and filters. The outputs of radiation sensors 42 and 44, and hence outputs of signal conditioners A1 and A3, represent the incident radiation levels $I_1$ and $I_2$, respectively, discussed above in connection with FIG. 1A.

According to one embodiment, the apparatus 10 additionally includes one or more circuits, shown in FIG. 3, for example, as a first circuit 56 (C1), a second circuit 52 (C2), a third circuit 54 (C3), and a fourth circuit 60 (C4). One or more circuits, such as the first second, third, and fourth circuits of FIG. 3, function essentially to determine the effectiveness of the sunscreen 26, and in particular the absorption coefficient $\beta_1$ of the sunscreen 26 to the first radiation 36, based on the incident and reflected levels of the first and second radiation, as discussed above in connection with FIG. 1A and Eq. (2).

As shown in the example of FIG. 3, outputs of the signal conditioners A1 and A2 are coupled to the second circuit 52, outputs of the signal conditioners A3 and A4 are coupled to the third circuit 54, an output of the third circuit 54 is coupled to the fourth circuit 60, and outputs of the second and fourth circuits are respectively coupled to the first circuit 56. In one embodiment, the third circuit 54 outputs a signal 154 based on a ratio of the reflected and incident second radiation 38, which gives a "baseline" measure of the absorption of the second radiation by the skin 24. In a similar manner, the second circuit 52 outputs a signal 152 based on a ratio of the reflected and incident first radiation 36, which gives a measure of the total absorption of the first radiation by both the sunscreen 26 and the skin 24.

As shown in FIG. 3, according to one embodiment, the signal 154, representing a measure of the absorption of the second radiation by the skin 24, is input to the fourth circuit 60 along with a compensation coefficient 58 (K1). The fourth circuit 60 outputs a signal 155 based on the signal 154 and the compensation coefficient 58. As discussed above in connection with FIG. 1A, the absorption by the skin 24 of the first radiation 36 and the second radiation 38 is well-correlated; however, this absorption may not be identical for both the first radiation 36 and the second radiation 38, depending upon the choice of wavelength ranges selected for the first and second radiation, respectively. Accordingly, the compensation coefficient 58 may be used to account for any differences in absorption by the skin of the first radiation 36 and the second radiation 38. In this manner, the signal 155 output by the fourth circuit 60 may more accurately represent a measure of the absorption of the first radiation 36 by the skin 24.

The signals 152 and 155, output respectively by the second and fourth circuits 52 and 60 in FIG. 3, are input to the first circuit 56, which in turn outputs a signal 156 based on a ratio of the input signals 152 and 155. Essentially, the first circuit 56 compares the absorption of the first radiation 36 by both the sunscreen 26 and the skin 24 to the absorption of the first radiation 36 by the skin 24 to determine the absorption of the first radiation 36 by only the sunscreen 26.

Examples of one or more circuits, such as the first, second, third, and fourth circuits 56, 52, 54, and 60 suitable for implementing the apparatus 10 shown in FIG. 3 include, but are not limited to, analog comparators such as subtractor or divider circuits, as well as programmable logic devices, that perform the various signal operations to derive the effectiveness of the sunscreen 26, as discussed above. Additionally, in one embodiment, the first, second, third, and fourth circuits may be replaced by one or more processors, which may include one or more analog to digital converters, and which may be programmed to calculate the effectiveness of the sunscreen 26 based on the measured parameters represented by the signals output from the signal conditioners A1, A2, A3, and A4. Numerous other implementations are possible, and the present invention is not limited to these or any specific implementations.

In the embodiment shown FIG. 3, the incident first and second radiation 36B and 38B reflected by reflector 50 are detected by sensors 42 and 44, and signals representing the respective incident radiation levels are output by signal conditioners A1 and A3 to the second and third circuits 52 and 54. As discussed above, it should be appreciated, however, that in other embodiments in which the incident first and second radiation levels are measured externally to the apparatus 10, or are known based on known power output levels of internal or external sources, for example, signals representing the known levels may be input directly to the second and third circuits 52 and 54. Alternatively, in embodiments in which one or more processors or programmable logic devices are used in place of the first, second, third, and fourth circuits 56, 52, 54, and 60, any known incident radiation levels may be input and/or stored for use by a program to calculate the effectiveness of the sunscreen 26. In embodiments where incident radiation levels are known or measured externally, it should be appreciated that the reference sensors 42 and 44, the reflector 50, the radiation path 40, and the second and third circuits 52 and 54, may not be required.

FIG. 3 also shows that the indicator 16, as shown in FIG. 1B on the front panel 12 of the apparatus 10, is coupled to the first circuit 56. The indicator 16 receives the output signal 156 from the first circuit 56, and indicates an effectiveness of the sunscreen 26 based on the output signal 156. As shown in FIG. 3, according to one embodiment the indicator 16 may indicate in the form of a bar-graph, wherein a magnitude of the darkened "bar" portion of the indicator 16 represents a magnitude of effectiveness; for example, the bar-graph of the indicator 16 shown in FIG. 3 indicates approximately 40% effectiveness.

In one embodiment, the indicator 16 may also indicate, using alpha-numeric symbols, an actual sun protection factor, or SPF, of the sunscreen 26 applied to the skin 24, based on the output signal 156. In yet another embodiment, discussed further below in connection with FIGS. 5–7, the indicator 16 may make a comparison of the effectiveness of the sunscreen 26 and a labeled SPF value associated with the sunscreen 26, and indicate a "sunscreen efficiency" based on the comparison of the actual effectiveness and the labeled protection factor.

It should be appreciated that the first, second, third, and fourth circuits 56, 52, 54, and 60 may perform their respective signal operations periodically, such that the indicator 16 may indicate a dynamic actual effectiveness of the sunscreen over time. Such a feature is particularly useful when considering the "time-delayed" characteristics of many sunscreens. Specifically, as discussed above, sunscreens generally do not become effective until they have dried to some extent after application.

Accordingly, an individual may use the apparatus 10 after application of the sunscreen and throughout a drying period of the sunscreen to determine the dynamic actual effectiveness of the sunscreen and, in particular, when the sunscreen becomes most effective as a protective agent against potentially harmful ultraviolet radiation. In one embodiment, the indicator 16 may include a differentiating circuit (not shown) to monitor a rate of change of the signal 156 output from the first circuit 56, which fluctuates or changes as the effectiveness of the sunscreen changes throughout the drying period. In such an embodiment, the indicator 16 may be designed to indicate when the rate of change of the signal 156 has reached a minimum value, thereby indicating that the effectiveness of the sunscreen has "stabilized."

While the foregoing discussion focussed primarily on determining the effectiveness of sunscreens that are designed to absorb ultraviolet radiation, in other embodiments, various methods and apparatus according to the invention may determine an effectiveness of sunscreens that are designed primarily to reflect ultraviolet radiation. In such embodiments, levels of the reflected first radiation 36A detected by the radiation sensor 32 would generally increase with increased effectiveness of a reflective-type sunscreen 26. This effect is opposite to that of the apparatus described above, in which levels of the reflected first radiation 36A detected by the radiation sensor 32 would generally decrease with increased effectiveness of an absorbing sunscreen 26. The circuits 52, 54, 56, and 60, or equivalents thereof, may be designed or selected to accommodate the relative signal strengths anticipated by embodiments directed to either absorbing or reflecting sunscreens, or both absorbing and reflecting sunscreens. In one embodiment, for example, the various components illustrated in FIG. 3, including the sensors 32, 34, 42, and 44, the signal conditioners A1–A4 and the circuits 52, 54, 56, and 60 may be designed or selected, and configured, such that an apparatus according to the invention is capable of automatically determining whether the sunscreen 26 is of an absorbing or reflecting type, and is capable of providing an accurate indication of effectiveness on the indicator 16 for either.

The schematic diagram of FIG. 3 also shows one of the solar batteries 14, which may be included in the apparatus 10, as illustrated in FIG. 1B. FIGS. 1B and 3 show that one or more solar batteries 14 are illuminated by the ambient radiation 100 impinging upon the front surface 12 of the apparatus 10. The one or more solar batteries 14 convert the ambient radiation 100 to electrical power, which may be distributed to various components of the apparatus, such as the signal conditioners A1–A4, the circuits 52, 54, 56, and 60, and the indicator 16.

Figure 4:
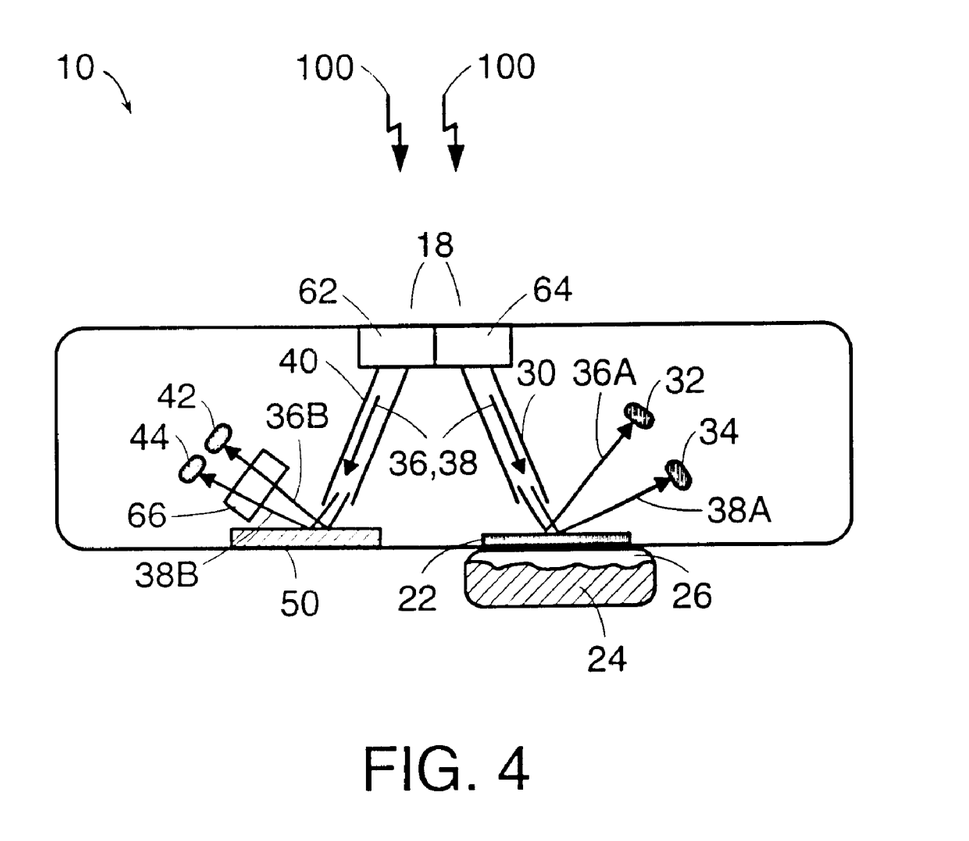
FIG. 4 is a diagram showing a side view of the apparatus of FIG. 1B, according to another embodiment of the invention.

FIG. 4 is a diagram showing a side view of the apparatus 10 of FIG. 1B, according to another embodiment of the invention. In the embodiment of FIG. 4, one or more modulators 62, 64, and 66 may be employed to differentiate any of the detected radiation 36A, 38A, 36B, and 38B from any background radiation inadvertently detected by the sensors 32, 34, 42, and 44, respectively. For example, background ambient radiation may inadvertently reach the detectors 32 and 34 through the skin window 22, in the event of an incomplete contact between the skin window 22 and the sunscreen 26 applied to the skin 24. In this case, the reference sensors 42 and 44 may not accurately indicate the level of first radiation 36 and second radiation 38 incident to the sunscreen 26 and the skin 24, for these sensors would not be accounting for the background ambient radiation entering through the skin window 22.

Accordingly, various modulation techniques may be utilized in the embodiment of FIG. 4 to improve signal-to-noise ratios between desired signals and any undesired signals due to, for example, background ambient radiation or other noise, such as thermal noise, detected or generated by the sensors 32, 34, 42, and 44. In particular, modulation techniques such as, for example, amplitude modulation, phase modulation, or frequency modulation may be employed by one or more of the modulators 62, 64, and 66. Examples of modulators suitable for purposes of the invention include, but are not limited to, a variety of shutters, including rotating shutters, acousto-optic modulators and electro-optic modulators.

Additionally, various modulation techniques may be employed in the embodiment of FIG. 4 to facilitate the use of one wide-band sensor in place of either the radiation sensors 32 and 34, and/or the reference sensors 42 and 44. Unlike the case of individual sensors for the first and second radiation, respectively, where signals representing the first and second radiation are output on physically separate lines, the signals output from a wide-band sensor sensitive to both the first and second radiation are typically output together on a single line. Accordingly, modulation techniques can assist in "separating" these signals into their constituent components representing each of the first and second radiation.

To accomplish the separation of signals output from a wide-band sensor, one of the first radiation 36 or the second radiation 38 may be modulated. In this manner, the signal component output by the wide-band sensor corresponding to the modulated radiation will itself be modulated. Subsequent conditioning of the various signal components output by the wide-band sensor can therefore "recover" the modulated component of the signal separately from the umnodulated component.

For example, in embodiments employing one or more wide-band sensors and one or more modulators 62, 64, and 66, the signal conditioners A1–A4 or the circuits 52, 54, 56, and 60, illustrated in FIG. 3, may include one or more demodulators (not shown) to demodulate output signals from one or more wide-band sensors, in order to differentiate the signal component representing the modulated first or second radiation from the unmodulated component. Alternatively, the outputs of one or more wide-band sensors may pass through one or more discrete demodulators (not shown), prior to the signal conditioners A1–A4 shown in FIG. 3, to differentiate the signals representing the modulated first or second radiation.

In other embodiments employing modulators to improve signal-to-noise ratios between desired signals and any undesired signals due to, for example, background ambient radiation or other noise, one or more discrete demodulators, or demodulators integrated with the signal conditioners A1–A4 or the circuits 52, 54, 56, and 60, may be similarly used to differentiate the modulated desired signals from the undesired background or noise signals.

As shown in FIG. 4, the apparatus 10 may includes one or more modulators 62, 64, and 66 to modulate one or both of the first radiation 36 and the second radiation 38. For example, as shown in FIG. 4, the modulator 64 may modulate one or both of the first radiation 36 and the second radiation 38 directed by the first radiation path 30, through the skin window 22 to the sunscreen 26 and the skin 24. According to this embodiment, at least one of the reflected first radiation 36A and the reflected second radiation 38A is modulated.

Similarly, as shown in FIG. 4, the modulator 62 may modulate one or both of the first radiation 36 and the second radiation 38 directed by second radiation path 40 to the reference sensors 42 and 44. In one aspect of this embodiment, in addition to, or alternatively to, the modulator 62, the modulator 66 may modulate one or both of the reflected incident first radiation 36B and the reflected incident second radiation 38B. In yet another aspect of this embodiment, the reflector 50 itself may be constructed and arranged as a modulating reflector 50. Examples of modulating reflectors suitable for purposes of the invention include, but are not limited to, mechanical movable micromirror assemblies and electro-optic thin film reflectors.

As discussed above in connection with the embodiment shown in FIG. 2, in the embodiment of FIG. 4, the first radiation 36 and the second radiation 38 directed to the skin 24 and the sunscreen 26, as well as the reflector 50, may be provided by a single radiation source. For example, the first radiation 36 and the second radiation 38 may be derived essentially from the ambient radiation 100 as shown in FIG. 4 or, alternatively, the apparatus 10 may include one or more internal radiation sources (not shown) to generate the first radiation 36 and the second radiation 38 independently of the ambient radiation 100. In the case of one or more internal radiation sources, the internal sources themselves may include modulators, or outputs of the internal sources may be directed to, for example, one or both of the modulators 62 and 64.

In another embodiment, methods and apparatus according to the invention measure an ability of a region of an individual's skin to withstand exposure to harmful radiation, or a "total protection factor" of the region of skin with respect to exposure to harmful radiation. For example, according to one embodiment, the ability of an individual's skin to withstand exposure to harmful radiation may be measured in terms of an individual's own "natural" protection, or "skin darkness," as well as the effectiveness of any sunscreen that may be applied to the skin. Additionally, the ability of the skin to withstand exposure, whether or not sunscreen has been applied, may be periodically measured over time to determine a dynamic behavior of such ability with continued exposure to harmful radiation.

In a further embodiment of the invention, the level of harmful radiation to which the individual's skin is exposed is continually monitored and measured to determine a safe exposure time for the individual, based on any changes in the ability of the skin to withstand exposure, and any changes in environmental conditions that affect the level of harmful radiation. As a result, methods and apparatus of the invention provide an accurate dynamic indication of a safe exposure time for the individual.

Figure 5:
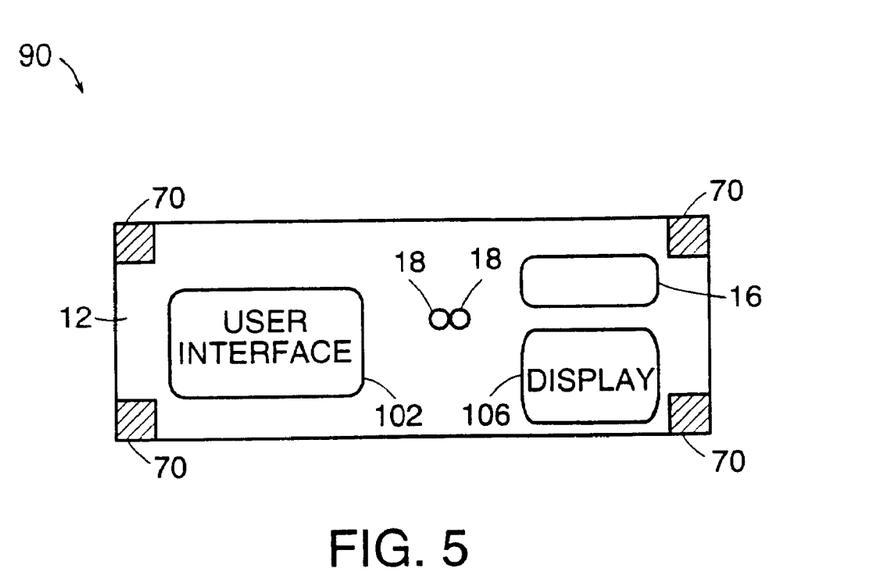
FIG. 5 is a diagram showing a top view of an apparatus for determining a safe exposure time of a region of skin to harmful radiation, according to one embodiment of the invention.

FIG. 5 is a diagram showing a top view of one illustrative embodiment of an apparatus 90 for determining a safe exposure time of a region of skin to harmful radiation. Similarly to the apparatus 10 shown in FIG. 1B, the apparatus 90 of FIG. 5 includes a front panel 12. The front panel 12 of the apparatus 90 may include one or more indicators 16 to indicate, for example, the ability of the individual's skin to withstand exposure to the harmful radiation. The indicator 16 may also, as in the apparatus 10 of FIG. 1B, indicate an effectiveness of sunscreen applied to the skin. In addition to the one or more indicators 16, FIG. 5 shows that the apparatus 90 may include one or more displays 106 to display a variety of other information provided by the apparatus 90, such as, for example, a safe exposure time, an elapsed time since a prior application of sunscreen, a reminder to reapply sunscreen, and the like.

FIG. 5 also shows that the apparatus 90 may include a user-interface 102, such as a keyboard or keypad, to permit a user to control the apparatus 90 and to input a variety of data such as, for example, a sunscreen SPF value to the apparatus 90. Additionally, the front panel 12 of the apparatus 90 may include one or more radiation path openings 18 which allow ambient radiation impinging upon the front panel 12 to enter the apparatus 90. Also, while not explicitly shown in FIG. 5 for purposes of clarity, the apparatus 90, as in the apparatus 10 of FIGS. 1–4, may include one or more solar batteries to provide power to various components of the apparatus 90.

Figure 6:
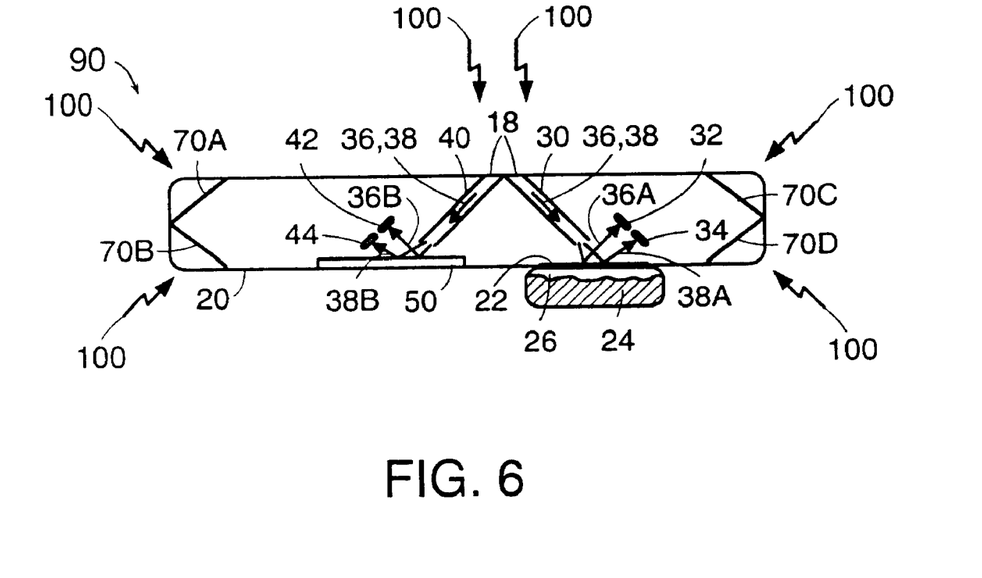
FIG. 6 is a diagram showing a side view of the apparatus of FIG. 5, according to one embodiment of the invention.

FIG. 6 is a diagram showing a side view of the apparatus of FIG. 5, looking through a "phantom" side panel of the apparatus 90 to various components within the apparatus 90. In several respects, the components illustrated in FIG. 6 are similar to those illustrated in the embodiment of the apparatus 10 illustrated in FIG. 2. Unlike the apparatus 10 of FIG. 2, however, FIG. 6 shows that the apparatus 90 includes one or more ambient radiation sensors 70, shown, for example, as corner sensors 70A, 70B, 70C, and 70D in FIG. 6.

While FIG. 6 shows the ambient radiation sensors 70 positioned at respective corners of the apparatus 90, two or more ambient radiation sensors may be spaced apart, or distributed partially or fully around, the apparatus 90 in a variety of positional arrangements. In one embodiment, two or more ambient radiation sensors 70 having planes of incidence at various orientations are employed to detect ambient radiation at a number of incidence angles. The ambient radiation sensors 70 may be arranged such that the ambient radiation 100 from several directions may be detected from various locations proximate to the skin.

By measuring the ambient radiation 100 at a number of different incidence angles from different directions and different locations proximate to the skin 24, the apparatus 90 can provide an accurate measurement of potentially harmful ambient radiation 100 that actually irradiates the skin 24. For example, while ambient radiation 100 may directly impinge upon skin 24 facing the source of the ambient radiation 100, for example, the sun, the ambient radiation 100 from the source may also be reflected off of a number of surfaces near the skin 24, for example, water, sand, snow, metallic objects associated with various sporting and recreational equipment, and the like. Often, the ambient radiation 100 reflected from various surfaces near the skin 24 is of a level equal to or greater than that of the direct ambient radiation 100 irradiating the skin 24. Accordingly, by accounting for both direct and reflected ambient radiation 100, the apparatus 90 accurately provides an actual total exposure level of the skin 24 to the ambient radiation 100.

Figure 7:
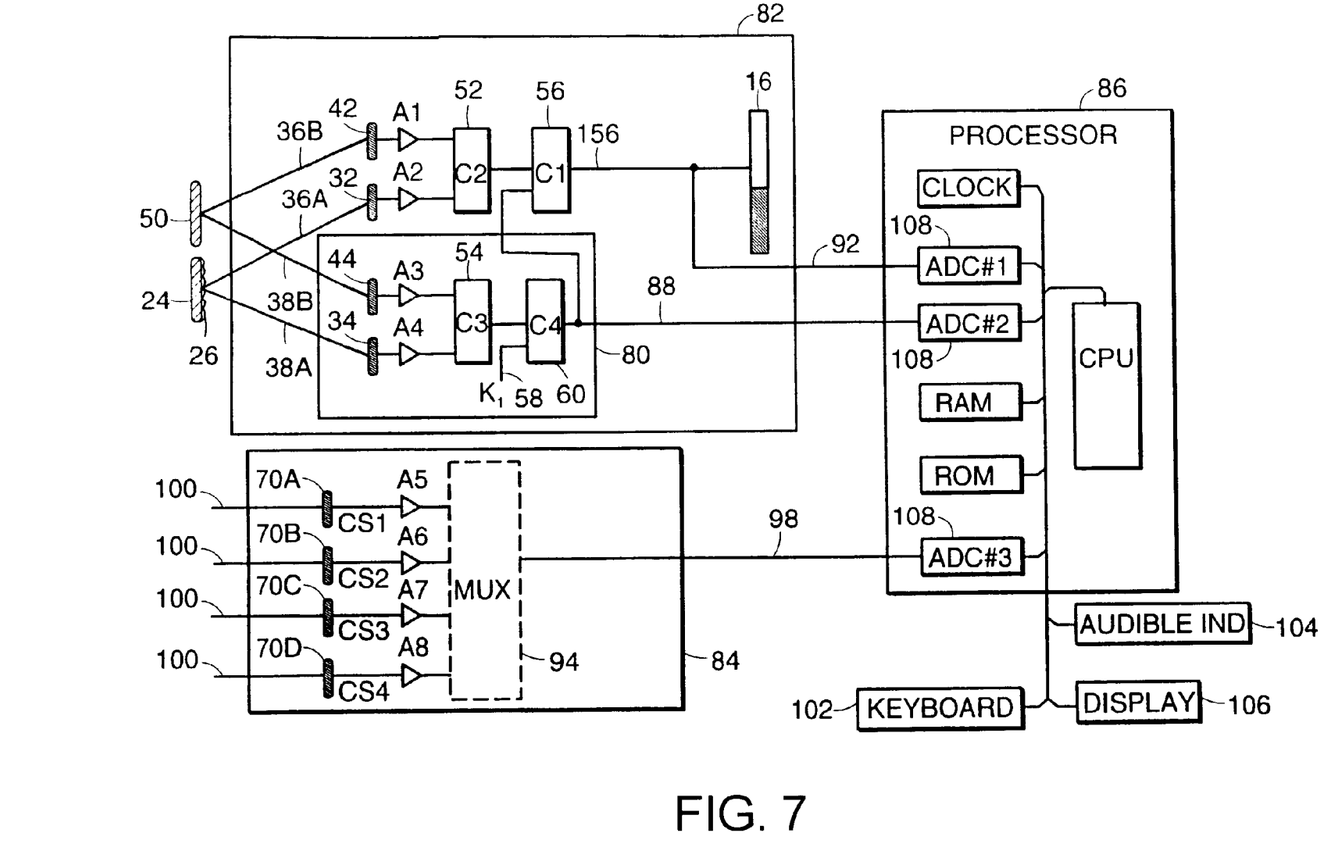
FIG. 7 is a schematic diagram showing various components of the apparatus of FIGS. 5 and 6, according to one embodiment of the invention.

FIG. 7 is a schematic diagram illustrating various components of the apparatus 90 shown in FIGS. 5 and 6. FIG. 7 shows that, according to one embodiment, the apparatus 90 of FIGS. 5 and 6 may include a skin darkness circuit 80 to measure a darkness of the skin 24, a sunscreen effectiveness circuit 82 (which includes the skin darkness circuit 80) to measure an effectiveness of any sunscreen 26 optionally applied to the skin 24, a total exposure circuit 84 to measure a total exposure level of the skin 24 to the ambient radiation 100, and a processor 86, coupled to the skin darkness circuit 80, the sunscreen effectiveness circuit 82, and the total exposure circuit 84, to calculate a safe exposure time based on the effectiveness of the sunscreen 26, the darkness of the skin 24 and the total exposure level 86. While FIG. 7 schematically shows only some of the components associated with the skin darkness circuit 80 and the sunscreen effectiveness circuit 82 for ease of illustration, it should be appreciated that, with reference to FIG. 6, the radiation paths 30 and 40 (not shown in FIG. 7) also constitute portions of both the skin darkness circuit 80 and the sunscreen effectiveness circuit 82.

For example, the skin darkness circuit 80, in addition to those components shown in FIG. 7, includes one or both of radiation paths 30 and 40 shown in FIG. 6. The skin darkness circuit 80 of the apparatus 90 utilizes only the second radiation 38 outside an absorption spectrum of any sunscreen 26 which may be applied to the skin 24.

As shown in FIG. 7, the third circuit 54, serving as a first skin darkness sub-circuit coupled to the reference sensor 44 and the radiation sensor 34 via the signal conditioners A3 and A4, compares the incident second radiation 38B and the second radiation 38A reflected from the skin 24 to output a skin darkness signal 88 to the processor 86. Since any applied sunscreen 26 does not significantly absorb the second radiation 38, the skin darkness signal 88 is primarily a function of the second radiation 38 absorbed by the skin 24.

The skin darkness circuit 80 essentially functions to compare the incident second radiation 38B and the second radiation 38A reflected from the skin 24 to determine the skin's reflection coefficient $\alpha_2$ which, as discussed above in connection with FIG. 1A, is a measure of the skin's ability to absorb the second radiation, and hence is a measure of the skin's "natural" protection factor. Accordingly, the skin darkness signal 88 may be used by the processor 86 to indicate an individual's natural protection factor relative to a number of accepted skin type classifications such as, for example, Type I or extremely sensitive skin. Additionally, the skin darkness signal 88 may be used by the processor to determine a "total protection factor," which may include not only the natural protection factor of the skin, but also the protection factor of any sunscreen applied to the skin.

FIG. 7 also shows that the apparatus 90 may include a sunscreen effectiveness circuit 82, which is similar to that of the apparatus 10 shown in FIGS. 1–4. As in various embodiments of the apparatus 10, while not explicitly shown in FIGS. 6 or 7, the sunscreen effectiveness circuit 82 may include one or more modulators to modulate one or both of the first radiation 36 and the second radiation 38. FIG. 7 shows that the sunscreen effectiveness circuit 82 outputs a sunscreen effectiveness signal 92 to both the processor 86 and the indicator 16.

In FIG. 7, according to one embodiment, an output of each ambient radiation sensor 70A, 70B, 70C, and 70D of the total exposure circuit 84 respectively passes to a signal conditioner A5, A6, A7, and A8, which may be similar to the single conditioners A1–A4 discussed above in connection with FIG. 3. Outputs of single conditioners A5–A8 are input to a multiplexer 94, and an output 98 of the multiplexer 94 is coupled to the processor 86. The multiplexer 94 couples each of the sensors 70A, 70B, 70C, and 70D to the processor 86, so that the processor may monitor signals from each of the sensors to provide a variety of information in connection with the ambient radiation.

For example, the processor 86 may calculate a sum of the signals output by the multiplexer 94 on output 98, representing the total exposure level of the skin 24 to the ambient radiation 100. Additionally, the processor 86 may calculate a peak exposure level of the ambient radiation based on signal outputs of one or more of the sensors 70. Furthermore, depending on the positions of two or more sensors 70 on the apparatus 90, the processor 86 may calculate and provide information relating to the directionality of radiation impinging on the apparatus, and in particular, from which direction the radiation is impinging most strongly on the apparatus, based on relative strengths of signals obtained from the individual detectors. In such embodiments, the processor 86 may, for example, provide some form of indication to a user, via, for example, the audible indicator 104 and/or the display 106, to inform the user to orient themselves in a different direction so as minimize exposure to radiation which is more strongly incident from a particular direction.

Alternatively, while not shown in FIG. 7, the outputs of the signal conditioners A5–A8 may be passed to a discrete summing circuit to sum the outputs of the signal conditioners, to provide a total exposure level signal to the processor 86. Similarly, the outputs of signal conditioners A5–A8 may pass to a discrete peak detector circuit which outputs a peak exposure signal to the processor. Furthermore, it should be appreciated that, according to one embodiment, the respective outputs of signal conditioners A5–A8 each may be directly input to the processor 86 so that a variety of information may be obtained from the individual sensors 70.

FIG. 7 also shows that the processor 86 may include a number of analog to digital converters 108 to receive the sunscreen effectiveness signal 92, the skin darkness signal 88, and the output signal 98 from the multiplexer 94. The processor 86 may also include a clock, various memories such as RAM and ROM, and a central processing unit, typical of many known processors. FIG. 7 also shows that the processor 86 is coupled to the user-interface 102 on the front panel 12 of apparatus 90, to receive user control information and data, and is also coupled to the display 106 and may also be coupled to an additional audible indicator 104, such as a beeper or a buzzer.

According to one embodiment, the apparatus 90 shown in FIGS. 5–7 functions essentially as follows. A user places the skin window 22 of the apparatus 90 over a region of the skin 24 and, for example, presses a "START" button on the user-interface 102. The skin darkness circuit 80 measures an initial skin darkness, or ability of the skin to withstand exposure to harmful radiation. The skin darkness circuit 80 measures the initial skin darkness irrespective of an application of sunscreen to the skin.

Additionally, according to one embodiment, the display 106 may indicate the measured skin darkness in terms of, for example, a "tanning level," based on a variety of informative scales. Furthermore, according to one embodiment, the apparatus 90 may store the initial skin darkness in memory, so that the initial skin darkness may be compared to skin darknesses measured at later times. In this manner, the apparatus 90 may indicate a comparative measure of cumulative tan, providing an individual with a measure of "tanning progress."

Moreover, according to one embodiment, a measure of cumulative tan over a control or "observation" period may be correlated to a cumulative total exposure level also measured during the observation period. Such a correlation could be stored in memory, and would allow the apparatus 90 to measure cumulative tan over arbitrary time periods and provide an indication to the user of a cumulative radiation dose, based on the correlation of cumulative tan to cumulative exposure. Since many forms of bodily damage may be characterized in terms of cumulative radiation dose, such information may be particularly useful to an individual in identifying potentially harmful levels of radiation to which they have been exposed over time.

If sunscreen is applied to the skin, the sunscreen effectiveness circuit 82 measures an initial sunscreen effectiveness. The apparatus 90 may determine whether the sunscreen 26 is of the reflective or the absorptive type, and displays the initial sunscreen effectiveness on the indicator 16, and/or on the display 106 as, for example, an actual SPF rating. In one embodiment, the user may enter, via the user-interface 102, a labeled sun protection factor (SPF) of the sunscreen, in which case the indicator 16 may indicate a sunscreen efficiency, based on the actual effectiveness of the sunscreen as compared to the labeled SPF of the sunscreen. The sunscreen effectiveness circuit 82 may additionally indicate to the processor 86 and/or the user whether or not the sunscreen has become effective, for example, after a drying period of the sunscreen after application. In turn, according to one embodiment, the processor 86 may sound an alarm via the audible indicator 104 to indicate sunscreen "stability," or the completion of a sufficient drying period.

In another embodiment, to differentiate measurements for which sunscreen has been applied from measurements in which no sunscreen is applied, the user may press, for example, a "CREAM" button, which initiates a measurement of the effectiveness of the sunscreen applied to the skin. In yet another embodiment, the sunscreen effectiveness may be measured automatically along with measurements of skin darkness. Furthermore, in one embodiment, the user may also enter, via the user-interface 102, a sunscreen application reminder period so that the processor 86 may indicate a periodic reminder, for example via audible indicator 104, to reapply sunscreen at intervals programmed by the user.

In addition to initial measurements performed by the skin darkness circuit 80 and the sunscreen effectiveness circuit 82 if sunscreen is applied to the skin, the total exposure circuit 84 detects the level of ambient radiation and provides multiplexer output signal 98 to the processor to determine the total exposure level. After measurements of the initial parameters of skin darkness, sunscreen effectiveness and total exposure level, the processor 86 then calculates an initial safe exposure time based on the skin darkness signal 88, the sunscreen effectiveness signal 92 if sunscreen has been applied, and the output signal 98 from the multiplexer 94, and displays the initial safe exposure time on the display 106. The safe exposure time may be indicated, for example, in terms of hours and minutes. In one embodiment, if sunscreen is applied, the processor 86 may wait to calculate the initial safe exposure time until after the drying period of the sunscreen.

Once the initial variables of skin darkness, sunscreen effectiveness, and total exposure levels are measured and an initial safe exposure time is determined, the processor 86 may continuously monitor the skin darkness signal 88, the sunscreen effectiveness signal 92 and the multiplexer output signal 98, and update the display of the safe exposure time based on any changes in these variables. Based on the time at which the "START" or "CREAM" buttons were pressed and a current safe exposure time, the processor 86 indicates when the current safe exposure time expires by, for example, sounding an alarm via the audible indicator 104 and/or displaying a message on the display 106.

The foregoing procedure may be repeated at any time, for example, after some exposure period of the skin to potentially harmful radiation, and/or upon first or subsequent applications of sunscreen, so that the user remains well-informed of safe exposure times to the potentially harmful radiation, based on current variables which affect the degree of protection afforded against such exposure. For example, as the individual's skin naturally darkens, if at all, generally longer safe exposure times would be indicated by the apparatus 90. Similarly, if a user applies sunscreen for the first time after some exposure period, reapplies sunscreen after a previous application, or applies a different sunscreen having a stronger sun protection factor, the apparatus 90 may indicate a longer safe exposure time.

From the foregoing, it should be appreciated that methods and apparatus according to various embodiments of the invention offer several advantages by providing real time information about the cumulative effects of exposure to potentially hail radiation, such as ultraviolet radiation, based on an individual's skin type and the actual effectiveness of any sunscreen applied on the individual's skin, independently of the labeled SPF value of the sunscreen. The effectiveness of the sunscreen and the skin darkness may be periodically measured over time to determine a dynamic behavior of the sunscreen and the skin with continued exposure to ultraviolet radiation. Accordingly, methods and apparatus of one embodiment of the invention provide a dynamic actual effectiveness of sunscreen applied to the skin of a particular individual, taking into account the particular individual's skin darkness, thereby providing an accurate indication of a safe exposure time for the individual, based on an accurate assessment of the total level of potentially harmful radiation to which the individual is exposed.

It should also be appreciated that methods and apparatus of the invention for determining the skin darkness of an individual, as well as methods and apparatus of the invention for detecting and measuring radiation at a number of different incidence angles from different directions and different locations to provide a total radiation exposure level, may be employed alone, or in combination with other methods and apparatus of the invention, to provide several advantages in connection with radiation measurements and/or an individual's response to exposure to radiation.

Having thus described certain embodiments of the present invention, various alterations, modifications and improvements will readily occur to those skilled in the art. Such alterations, modifications and improvements are intended to be within the spirit and scope of the invention. Accordingly, the foregoing description is by way of example only and not intended to be limiting. The invention is limited only as defined in the following claims and the equivalents thereof.

What is claimed is:

1. An apparatus, comprising:
    a first detector to detect an ability of a region of skin to withstand exposure to harmful radiation;
    a second detector to detect a level of the harmful radiation to which the region of skin is exposed;
    a first circuit, coupled to the first and second detectors, to calculate a safe exposure time based on the ability of skin to withstand the exposure to the harmful radiation and the level of the harmful radiation; and
    the first circuit periodically monitors the ability of the region of skin to withstand the exposure to the harmful radiation and the level of the harmful radiation detected by the first and second detectors, respectively, to periodically calculate a dynamic safe exposure time.

2. An apparatus, comprising:
    a first radiation path to direct first radiation and second radiation to a region of skin on which sunscreen has been applied, the first radiation having at least one first wavelength within an absorption spectrum of the sunscreen, the second radiation having at least one second wavelength not within the absorption spectrum of the sunscreen;
    at least one radiation sensor to detect the first radiation and the second radiation reflected from the region of skin;
    a first circuit, coupled to the at least one radiation sensor, to determine an effectiveness of the sunscreen based on the reflected first radiation and the reflected second radiation;
    an indicator, coupled to the first circuit, to indicate the effectiveness of the sunscreen;
    the first circuit periodically determines the effectiveness of the sunscreen based on the reflected first radiation and the reflected second radiation; and
    the indicator indicates a dynamic effectiveness of the sunscreen.

3. A method for determining a safe exposure time of a region of skin exposed to harmful radiation, comprising steps of:
    measuring an ability of the region of skin to withstand exposure to the harmful radiation;
    measuring a level of the harmful radiation;
    calculating a safe exposure time based on the ability of the region of skin to withstand the exposure to the harmful radiation and the level of the harmful radiation; and
    periodically repeating the steps of measuring the ability of the region of skin to withstand the exposure, measuring the level of the harmful radiation, and calculating the safe exposure time.

4. A method for determining an effectiveness of sunscreen applied to a region of skin, comprising steps of:
    irradiating the region of skin with first radiation having at least one first wavelength within an absorption spectrum of the sunscreen;
    irradiating the region of skin with second radiation having at least one second wavelength outside the absorption spectrum of the sunscreen;
    measuring a first reflected level of the first radiation reflected from the region of skin;
    measuring a second reflected level of the second radiation reflected from the region of skin;
    determining the effectiveness of the sunscreen based on the first reflected level and the second reflected level;
    the steps of irradiating with the first radiation, irradiating with the second radiation, measuring the first reflected level, measuring the second reflected level, and determining the effectiveness of the sunscreen are repeated periodically; and
    the method further includes a step of determining a dynamic effectiveness of the sunscreen over time.

5. A method for determining an effectiveness of sunscreen applied to a region of skin, comprising steps of:
    irradiating the region of skin with first radiation having at least one first wavelength within an absorption spectrum of the sunscreen;
    irradiating the region of skin with second radiation having at least one second wavelength outside the absorption spectrum of the sunscreen;
    measuring a first reflected level of the first radiation reflected from the region of skin;
    measuring a second reflected level of the second radiation reflected from the region of skin;

determining the effectiveness of the sunscreen based on the first reflected level and the second reflected level;

the step of determining the effectiveness of the sunscreen includes steps of:

measuring a first reference level of the first radiation incident to the region of skin;

measuring a second reference level of the second radiation incident to the region of skin;

calculating a first ratio of the first reflected level to the first reference level;

calculating a second ratio of the second reflected level to the second reference level;

calculating the effectiveness of the sunscreen as a third ratio of the second ratio to the first ratio;

periodically repeating the steps of irradiating with the first radiation, irradiating with the second radiation, measuring the first reflected level, measuring the second reflected level, measuring the first reference level, measuring the second reference level, calculating the first ratio, calculating the second ratio, and calculating the effectiveness of the sunscreen; and calculating a dynamic effectiveness of the sunscreen over time.

* * * * *